United States Patent
Liu et al.

(10) Patent No.: US 10,994,118 B2
(45) Date of Patent: May 4, 2021

(54) ANTIMICROBIAL STOPCOCK MEDICAL CONNECTOR

(71) Applicant: Becton, Dickinson and Company, Franklin Lakes, NJ (US)

(72) Inventors: Huibin Liu, West Jordan, UT (US); Bryan Fred Bihlmaier, Provo, UT (US); Janice Lin, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/184,735

(22) Filed: Nov. 8, 2018

(65) Prior Publication Data

US 2019/0099594 A1 Apr. 4, 2019

Related U.S. Application Data

(63) Continuation of application No. 14/260,037, filed on Apr. 23, 2014, now Pat. No. 10,149,971.

(51) Int. Cl.
*A61M 39/22* (2006.01)
*F16K 11/085* (2006.01)

(52) U.S. Cl.
CPC ........ *A61M 39/22* (2013.01); *A61M 2039/229* (2013.01); *A61M 2205/0205* (2013.01); *F16K 11/0853* (2013.01)

(58) Field of Classification Search
CPC .......... A61M 39/162; A61M 2039/229; A61M 2205/0205; F16K 11/08
See application file for complete search history.

(56) References Cited

U.S. PATENT DOCUMENTS

| 4,540,025 A | 9/1985 | Ledeen et al. |
| 4,932,948 A | 6/1990 | Kernes et al. |

(Continued)

FOREIGN PATENT DOCUMENTS

| CN | 1242781 | 1/2000 |
| CN | 102472401 | 5/2012 |

(Continued)

OTHER PUBLICATIONS

Merriam Webster (available online at https://www.merriam-webster.com/dictionary/proximal, accessed Jul. 23, 2019) (Year: 2019).

*Primary Examiner* — Manuel A Mendez
*Assistant Examiner* — Justin L Zamory
(74) *Attorney, Agent, or Firm* — Kirton & Mcconkie; Craig Metcalf; Kevin Stinger

(57) ABSTRACT

Various embodiments of an antimicrobial stopcock medical connector is provided. More specifically, the present invention relates to a stopcock tap having fluid channels provided on portions of the outer surface of the stopcock tap, whereby fluid bypasses the stopcock through the fluid channels by flowing between the outer surface of the stopcock tap and the inner surface of the stopcock housing. Some embodiments further comprise an antimicrobial coating or insert that is provided in the one or more fluid channel, whereby fluid flowing through the fluid channels contacts the antimicrobial coating or an antimicrobial agent that is eluted from the antimicrobial coating. Further still, some embodiments of the present invention comprise an antimicrobial groove that is positioned opposite the fluid channel, whereby when the stopcock is in an "off" position, the antimicrobial groove contacts fluid within a blocked port thereby preventing microbial growth therein.

2 Claims, 7 Drawing Sheets

(56) References Cited

U.S. PATENT DOCUMENTS

| | | |
|---|---|---|
| 5,046,528 A | 9/1991 | Manska |
| 5,135,026 A | 8/1992 | Manska |
| 5,203,775 A | 4/1993 | Frank et al. |
| 5,354,267 A | 10/1994 | Niermann et al. |
| 5,680,889 A | 10/1997 | Boger |
| 6,171,287 B1 | 1/2001 | Lynn et al. |
| 6,706,022 B1 | 3/2004 | Leinsing et al. |
| 7,033,339 B1 | 4/2006 | Lynn |
| 7,184,825 B2 | 2/2007 | Leinsing et al. |
| 7,232,428 B1 | 6/2007 | Inukai et al. |
| 7,771,383 B2 | 8/2010 | Truitt et al. |
| 8,048,034 B2 | 11/2011 | Eversull et al. |
| 8,591,471 B1 | 11/2013 | Marble |
| 8,715,222 B2 | 5/2014 | Truitt et al. |
| 2003/0199835 A1 | 10/2003 | Leinsing et al. |
| 2004/0013703 A1 | 1/2004 | Ralph et al. |
| 2004/0089834 A1 | 5/2004 | Koshima et al. |
| 2006/0016496 A1 | 1/2006 | Shane |
| 2006/0089603 A1 | 4/2006 | Truitt et al. |
| 2007/0083188 A1 | 4/2007 | Grandt et al. |
| 2007/0119968 A1 | 5/2007 | Collins et al. |
| 2007/0287953 A1 | 12/2007 | Ziv et al. |
| 2008/0161763 A1 | 7/2008 | Harding et al. |
| 2008/0194707 A1 | 8/2008 | Potter |
| 2008/0215021 A1 | 9/2008 | Cisko, Jr. et al. |
| 2009/0182309 A1 | 7/2009 | Muffly |
| 2010/0106102 A1 | 4/2010 | Ziebol et al. |
| 2010/0135949 A1 | 6/2010 | Ou-Yang |
| 2011/0257606 A1 | 10/2011 | Truitt et al. |
| 2012/0083750 A1 | 4/2012 | Sansoucy |
| 2012/0103448 A1 | 5/2012 | Hopf et al. |
| 2013/0012915 A1 | 1/2013 | Hopf et al. |
| 2013/0274686 A1 | 10/2013 | Ziebol et al. |
| 2014/0155844 A1 | 6/2014 | Isch et al. |
| 2014/0174578 A1 | 6/2014 | Bonnal et al. |
| 2014/0228466 A1 | 8/2014 | Lin et al. |
| 2014/0323970 A1 | 10/2014 | Duncan |
| 2015/0126699 A1 | 5/2015 | Yarrison et al. |
| 2015/0231307 A1 | 8/2015 | Shevgoor et al. |
| 2015/0231309 A1 | 8/2015 | Bihlmaier et al. |
| 2015/0306370 A1 | 10/2015 | Liu et al. |
| 2016/0008569 A1 | 1/2016 | Harding |
| 2016/0213911 A1 | 7/2016 | Liu et al. |

FOREIGN PATENT DOCUMENTS

| | | |
|---|---|---|
| CN | 103013094 | 4/2013 |
| DE | 1328095 | 2/1995 |
| DE | 19728562 | 2/1999 |
| DE | 102009050590 | 4/2011 |
| EP | 0166375 | 1/1986 |
| EP | 0410898 | 1/1991 |
| EP | 1234596 | 8/2002 |
| FR | 2791114 | 7/2002 |
| GB | 1249484 | 10/1971 |
| GB | 1262428 | 2/1972 |
| JP | 63-020344 | 1/1988 |
| JP | 02-234767 | 9/1990 |
| JP | 03-029664 | 2/1991 |
| JP | H08-508421 | 9/1996 |
| JP | 08-280788 | 10/1996 |
| JP | H11-70163 | 3/1999 |
| JP | 2005530547 | 10/2005 |
| JP | 2008-511371 | 4/2008 |
| JP | 2008-517653 | 5/2008 |
| JP | 2010-029381 | 2/2010 |
| JP | 2010-179031 | 8/2010 |
| JP | 2012-075901 | 4/2012 |
| JP | 2012-523300 | 10/2012 |
| JP | 2017513633 | 6/2017 |
| JP | 2019155182 | 9/2019 |
| WO | 94/22522 | 10/1994 |
| WO | 97/35634 | 10/1997 |
| WO | 2006/077951 | 7/2006 |
| WO | 2011/006934 | 1/2011 |
| WO | 2015/126699 | 8/2015 |
| WO | 2015/164130 | 10/2015 |
| WO | 2015/164134 | 10/2015 |

ANTIMICROBIAL STOPCOCK MEDICAL CONNECTOR

RELATED APPLICATIONS

This Application is a continuation of U.S. patent application Ser. No. 14/260,037, filed Apr. 23, 2014, and titled ANTIMICROBIAL STOPCOCK MEDICAL CONNECTOR, which is incorporated herein by reference.

BACKGROUND OF THE INVENTION

Infusion therapy generally involves the administration of a medication intravenously. When performing a typical infusion therapy, one or more infusion therapy device (e.g. tubing sets, catheters, etc.) are commonly used. In some instances, an infusion therapy device may include a stopcock medical connector to permit selective administration of a fluid through the infusion therapy device. The stopcock medical connector comprises a housing in which is rotatably seated a tap. The tap includes a fluid pathway that may be aligned (i.e., the open position) or misaligned (i.e., the closed position) within the housing to permit or prevent a fluid from passing through the housing. Thus, when administration of fluid is desired, the tap is rotated from the closed position to the open position to permit fluid to pass through the housing and into the patient via the infusion therapy device. Conversely, the tap is rotated to the closed position when it is desired to cease the administration of a fluid.

When in the closed position, fluid trapped within the fluid pathway of the stopcock medical connector remains stagnant and isolated from the remaining fluid within the infusion therapy device. Fluid within the infusion therapy device is also stagnant when in the closed position. These stagnant conditions are ideal for growth and colonization of microbes, which may lead to subsequent microbial infection when the medical connector is opened and the fluid is infused into the patient.

Thus, while methods and systems currently exist for selectively administering fluid to a patient via the use of a stopcock medical connector, challenges still exist. Accordingly, it would be an improvement in the art to augment or replace current techniques with the systems and methods discussed herein.

BRIEF SUMMARY OF THE INVENTION

The present invention relates to various antimicrobial stopcock medical connectors. More specifically, the present invention is related to systems and methods for providing an antimicrobial stopcock medical connector. The present invention is further related to a stopcock tap having fluid channels provided on portions of the outer surface of the stopcock tap, whereby fluid bypasses the stopcock through the fluid channels by flowing between the outer surface of the stopcock tap and the inner surface of the stopcock housing. Some embodiments further comprise an antimicrobial coating or insert that is provided in the one or more fluid channel, whereby fluid flowing through the fluid channels contacts the antimicrobial coating or an antimicrobial agent that is eluted from the antimicrobial coating. Further still, some embodiments of the present invention comprise an antimicrobial groove that is positioned opposite the fluid channel, whereby when the stopcock is in an "off" position, the antimicrobial groove contacts fluid within a blocked port thereby preventing microbial growth therein.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention relates to various antimicrobial stopcock medical connectors. More specifically, the present invention is related to systems and methods for providing an antimicrobial stopcock medical connector. The present invention is further related to a stopcock tap having fluid channels provided on portions of the outer surface of the stopcock tap, whereby fluid bypasses the stopcock through the fluid channels by flowing between the outer surface of the stopcock tap and the inner surface of the stopcock housing. Some embodiments further comprise an antimicrobial coating or insert that is provided in the one or more fluid channel, whereby fluid flowing through the fluid channels contacts the antimicrobial coating or an antimicrobial agent that is eluted from the antimicrobial coating. Further still, some embodiments of the present invention comprise an antimicrobial groove that is positioned opposite the fluid channel, whereby when the stopcock is in an "off" position, the antimicrobial groove contacts fluid within a blocked port thereby preventing microbial growth therein.

Figure 1:
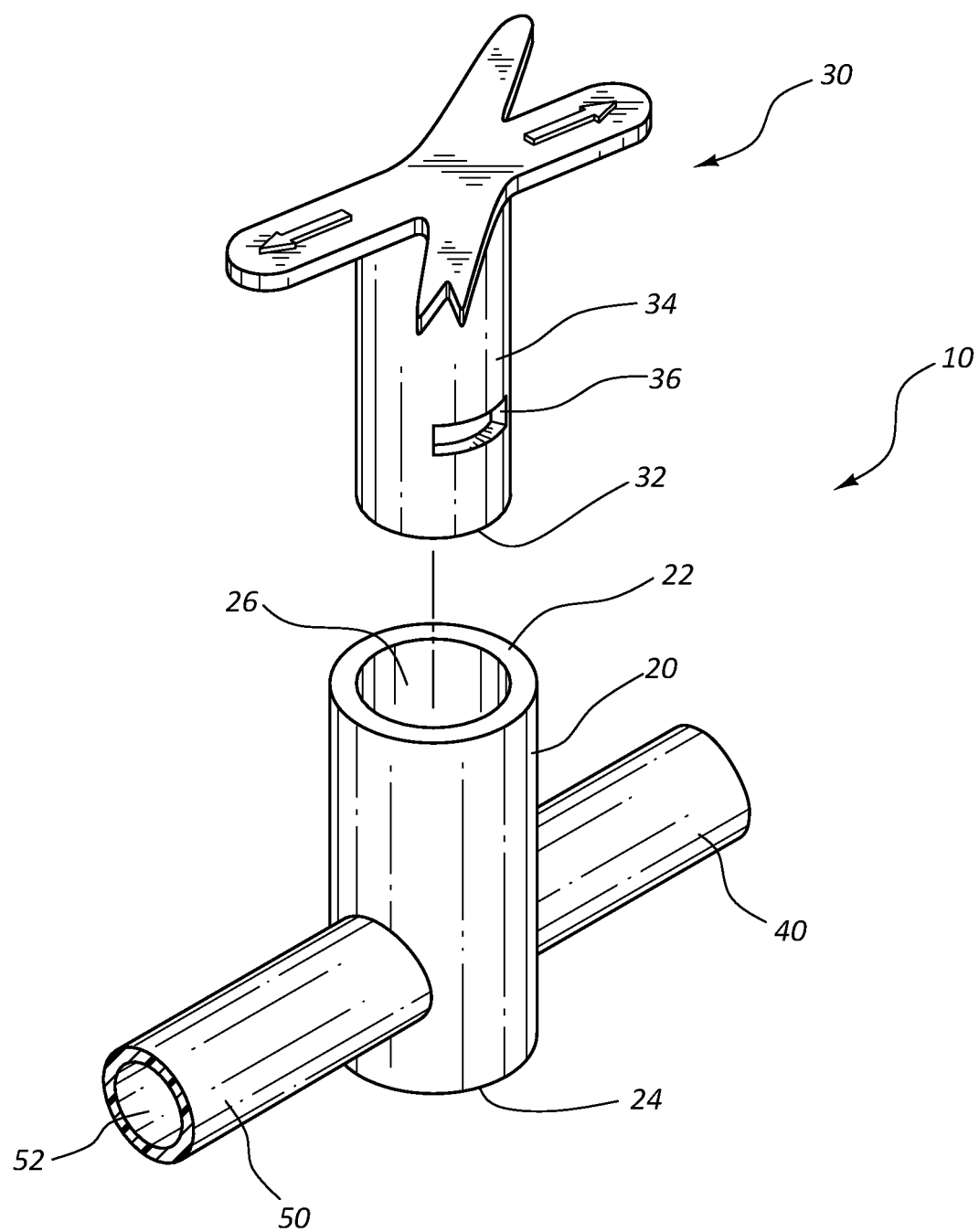
FIG. 1 shows a perspective, exploded view of an antimicrobial stopcock medical connector in accordance with a representative embodiment of the present invention.

Referring now to FIG. 1, an exploded, perspective view of a stopcock medical connector 10 is shown. Stopcock medical connector 10 comprises a housing 20 generally having a tubular shape. Housing 20 comprises an opening or proximal end 22 that is sized to compatibly receive tap 30. In some instances, housing comprises a side port of an intravenous device, such as a catheter adapter. Housing 20 further comprises a closed or distal end 24 that is located opposite opening 22, wherein housing 20 comprises a lumen 26 extending between proximal and distal ends 22 and 24. In some instances, distal end 24 further provides a seat surface that is configured to support tap 30 when seated within lumen 26.

In some instances, housing 20 further comprises one or more ports that are connected to housing 20 and in fluid communication with lumen 26. For example, in some embodiments housing 20 comprises an upstream port 40 and a downstream port 50. Upstream and downstream ports 40 and 50 each comprise a hollow interior, 42 and 52, respectively, that is in fluid communication with lumen 26. The free ends of ports 40 and 50 may be coupled to an intravenous device, such as a section of intravenous tubing, or a syringe. Fluid within upstream port 40 may pass into downstream port 50 by passing through lumen 26. Further, a fluid within lumen 26 may pass through either upstream or downstream ports 40 and 50, depending upon the desired direction of flow.

Stopcock tap 30 is configured to compatibly insert within lumen 26, whereby the base 32 of tap 30 is seated against the inner surface of distal end 24 when tap 30 is fully inserted within housing 20. Tap 30 is rotatably seated within lumen 26. A fluid tight seal is further established between shaft 34 of tap 30 and lumen 26, whereby fluid within lumen 26 is prevented from exited opening 22 when tap 30 is seated therein. In some instances, a hydrophobic lubricant, such as silicone grease, is inserted between shaft 34 and the inner surface of housing 20, thereby establishing the fluid tight seal. In other instances, proximal opening 22 comprises a mechanical seal, such as an o-ring, which established a fluid tight seal against shaft 34.

Shaft 34 comprises a circumference that is slightly less than the circumference of lumen 26. As such, shaft 34 may be inserted within lumen 26 with minimal tolerance. When inserted within lumen 26, the minimal tolerance between the outer surface of shaft 34 and the inner surface of lumen 26 prevents fluid from passing between upstream and downstream ports 40 and 50.

The outer surface of shaft 34 further comprises one or more fluid channels 36. In some instances, channels 36 comprise a groove forming a recess. Channels 36 comprise a length that is less than the circumference of shaft 34. In some instances, shaft 34 comprises a single channel 36 comprising a length that is less than half the circumference of shaft 34. In other instances, shaft 34 comprises two channels 36, each channel comprising a length that is less than one-third the circumference of shaft 34. Further, in some embodiments shaft 34 comprises three channels 36, each channel comprising a length that is less than one-fourth the circumference of shaft 34.

Figure 2A:
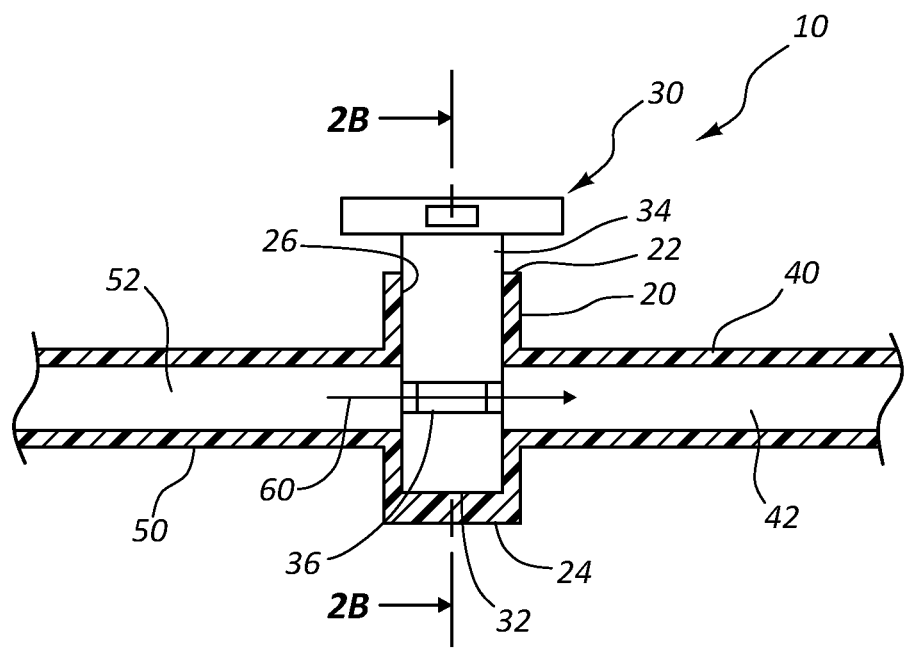
FIG. 2A shows a cross-section view of an antimicrobial stopcock medical connector in an opened position in accordance with a representative embodiment of the present invention.
Figure 2B:
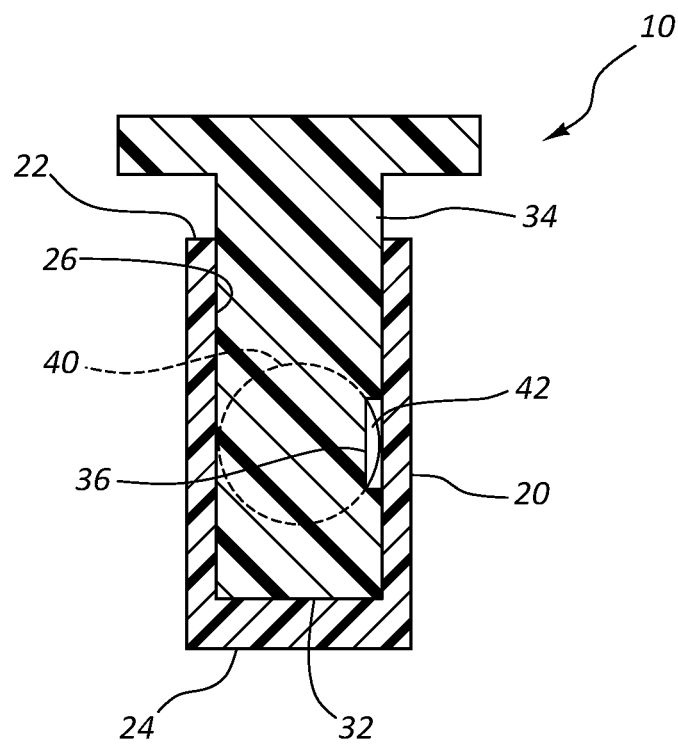
FIG. 2B shows another cross-section view of the antimicrobial stopcock medical connector of FIG. 2A in the opened position in accordance with a representative embodiment of the present invention.
Figure 3A:
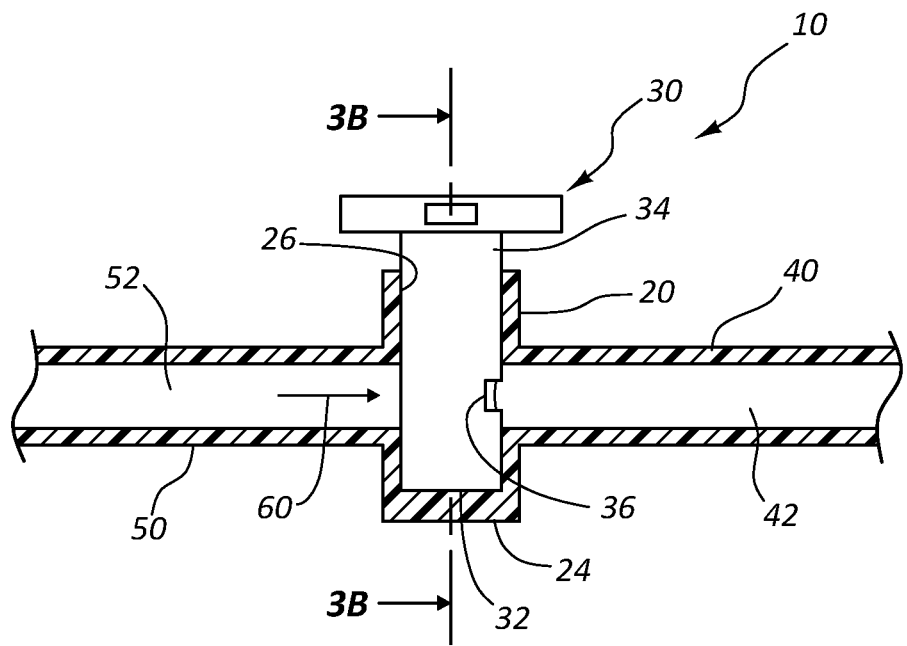
FIG. 3A shows a cross-section view of an antimicrobial stopcock medical connector in a closed position in accordance a representative embodiment of the present invention.
Figure 3B:
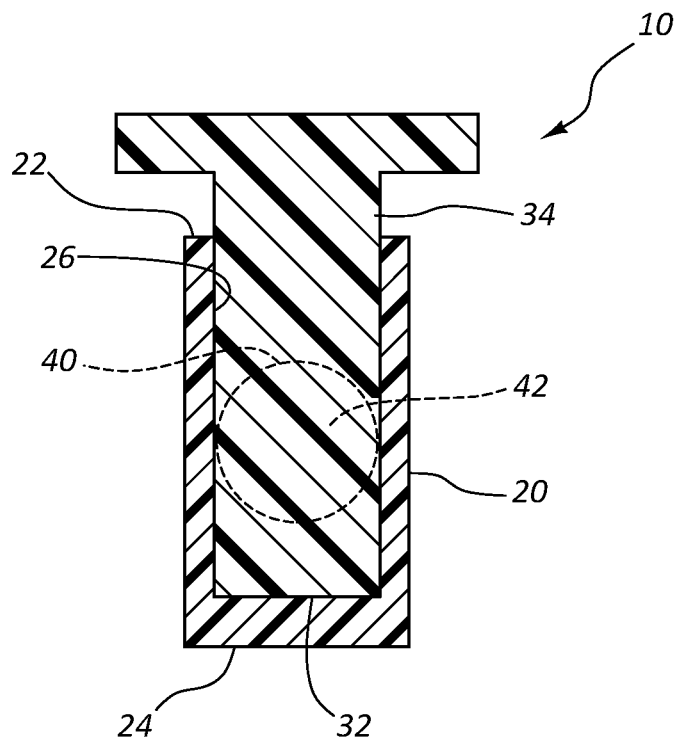
FIG. 3B shows another cross-section view of the antimicrobial stopcock medical connector of FIG. 3A in the closed position in accordance a representative embodiment of the present invention.

Shaft 34 may be rotated within lumen 26 to change the axial position of channels 36 within lumen 26. In some instances, shaft 34 is rotated within lumen 26 such that channels 36 are in simultaneous contact with the hollow interiors of upstream and downstream ports 40 and 50, as shown in FIGS. 2A, 2B and 4B. As such, channels 36 provide a fluid pathway between shaft 34 and the inner surface of lumen 26, thereby permitting fluid to flow between the hollow interiors 42 and 52. When shaft 34 is rotated within lumen 26 such that channels 36 are in contact with only one hollow interior, or no hollow interiors, fluid is prevented from bypassing shaft 34, as shown in FIGS. 3A-4A. Thus, selective flow of fluid 60 between upstream and downstream ports 40 and 50 may be achieved by rotating shaft 34 within lumen 26.

Figure 4A:
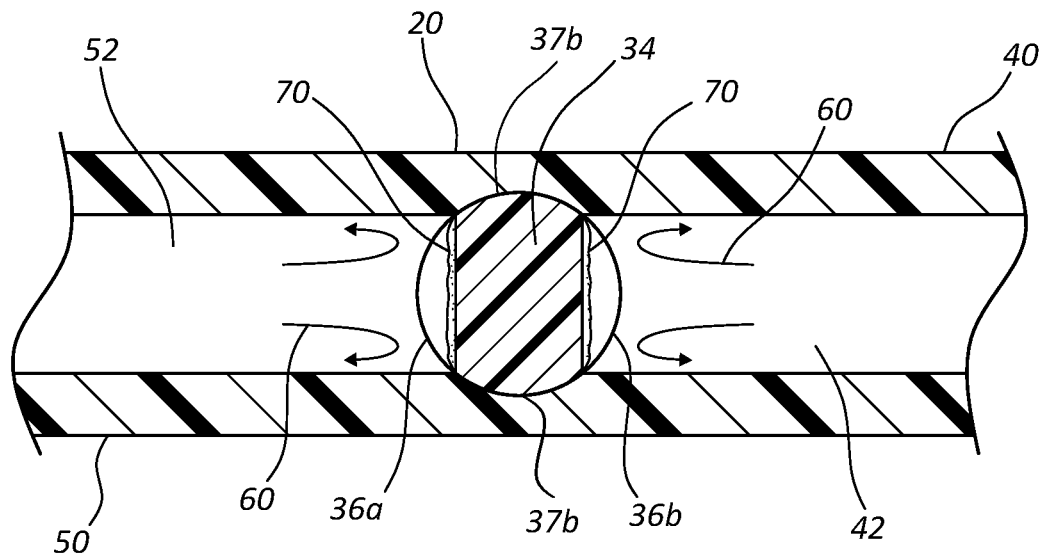
FIG. 4A shows a cross-section top view of an antimicrobial stopcock medical connector in a closed position in accordance with a representative embodiment of the present invention.
Figure 4B:
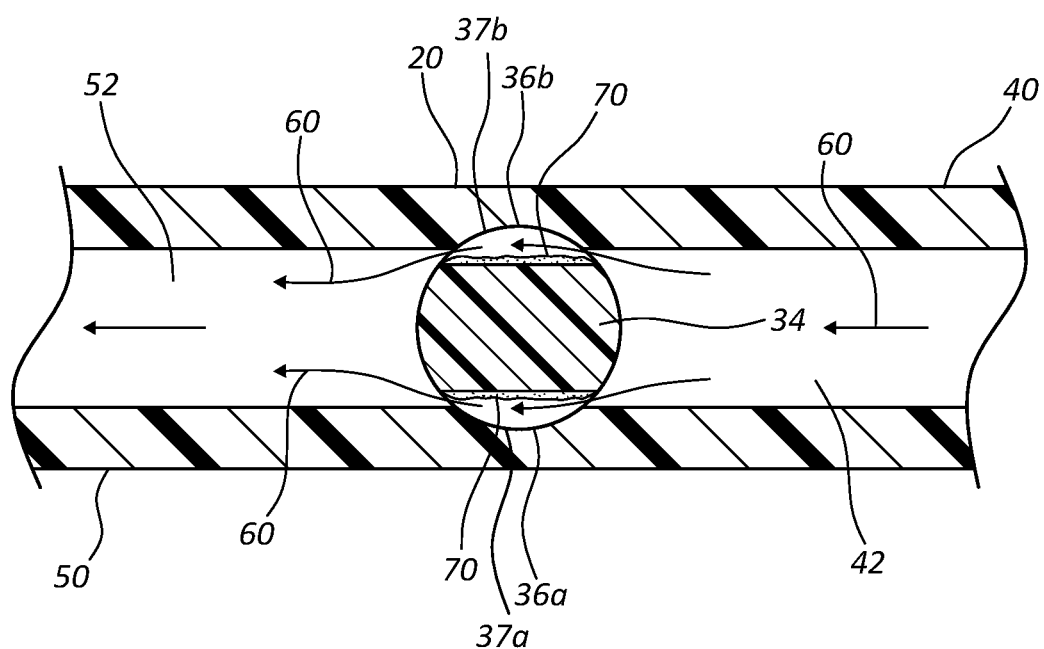
FIG. 4B shows another cross-section top view of the antimicrobial stopcock medical connector of FIG. 4A in an open position in accordance with a representative embodiment of the present invention.

Referring now to FIGS. 4A and 4B, in some embodiments shaft 34 comprises a first fluid channel 36a and a second fluid channel 36b, each channel having a length that is less than one-half the circumference of shaft 34. Channels 36a and 36b further comprise an antimicrobial coating 70.

Antimicrobial coating 70 is an agent that kills microorganisms or inhibits their growth. Antimicrobial coating 70 may comprise any material or combination of materials that are compatible for intravenous use. In some instances, antimicrobial coating 70 comprises any type or form of antimicrobial material that is safe for use in accordance with the teachings of the present invention. For example, in some instances antimicrobial material 70 is selected from a group consisting of chlorhexidine diacetate, chlorhexidine gluconate, alexidine, silver sulfadiazine, silver acetate, silver citrate hydrate, cetrimide, cetyl pyridium chloride, benzalkonium chloride, o-phthalaldehyde, and silver element.

In some instances, antimicrobial coating 70 comprises an insoluble, cured coating. In other instance, antimicrobial coating 70 comprises a cured coating that is softened when exposed to fluid, thereby eluting a portion of the antimicrobial agent into the fluid. Further, in some instances antimicrobial coating 70 comprises a cured material forming a matrix in which an antimicrobial agent is loaded. Upon exposure to a fluid, the antimicrobial agent is slowly eluted from the matrix, thereby providing an antimicrobial zone of inhibition around the coated surfaces. Further still, in some instances antimicrobial coating 70 comprises a soluble coating that slowly dissolves upon prolonged exposure to a fluid.

In some instances, antimicrobial coating 70 comprises an antimicrobial insert that is inserted into fluid channels 36. The antimicrobial insert may comprise any compatible material. In some instances, the antimicrobial insert comprises a compatible polymer material that is coated with an antimicrobial agent or coating. In other instances, the antimicrobial insert comprises an antimicrobial material that configured for insertion within fluid channel 36. An antimicrobial material may include a polymer material that is prepared in combination with an antimicrobial agent, whereby the final material comprises antimicrobial properties. For example, in some instances the final material exhibits antimicrobial activity through direct contact with a fluid. In some instances, the antimicrobial insert comprises a metallic material, such as elemental silver.

In other instances, the final material elutes antimicrobial agent when contacted by a fluid, thereby providing a zone of inhibition surrounding the material. For example, in some embodiments antimicrobial material 70 comprises a UV cured, hydrophilic polymer material that forms a matrix comprising a plurality of microscopic interstices in which an antimicrobial agent is dispersed (not shown). Upon exposure to fluid 60, the polymer matrix is softened and penetrated by the fluid. The antimicrobial agent within the polymer matrix is eluted out of the matrix and into the fluid to form a zone of inhibition in proximity to the polymer matrix. Examples of suitable polymer materials are provided in U.S. patent application Ser. Nos. 12/397,760, 11/829,010, 12/476,997, 12/490,235, and 12/831,880, each of which is incorporated herein in their entireties.

With specific reference to FIG. 4A, shaft 34 is shown in an axial position where channels 36a and 36b are each in contact with only one hollow interior, i.e. 52 and 42, respectively, thereby preventing fluid 60 from bypassing shaft 34. The antimicrobial coating 70 in each fluid channel 36a and 36b is in direct contact with fluid 60, whereby preventing microbial colonization and/or growth in the stagnant fluid.

Upon rotation of shaft 34, channels 36a and 36b contact both upstream and downstream ports 40 and 50, thereby permitting fluid 60 to flow freely therebetween, as shown in FIG. 4B. The housing 20 includes a first groove 37a and a second groove 37b. As fluid 60 passes through channels 36a and 36b, fluid 60 contacts antimicrobial coating 70, thereby preventing microbial growth and/or colonization on the coated surfaces. In some instances, antimicrobial agent within coating 70 is eluted from coating 70, thereby treating fluid 60 and providing a zone of inhibition around the coating channels 36.

Channels 36 may comprise any cross-section area to achieve a desired flow rate between upstream and downstream ports 40 and 50. In some instances, the combined cross-section areas of channels 36a and 36b are equal to the cross-section area of upstream or downstream ports 40 and 50. Where channels 36 comprise an antimicrobial coating 70, the combined cross-section area of the channel and the antimicrobial area are selected to ensure a desired rate of flow through device 10. Thus, channels 36 do not impede the rate of flow for device 10.

Figure 5A:
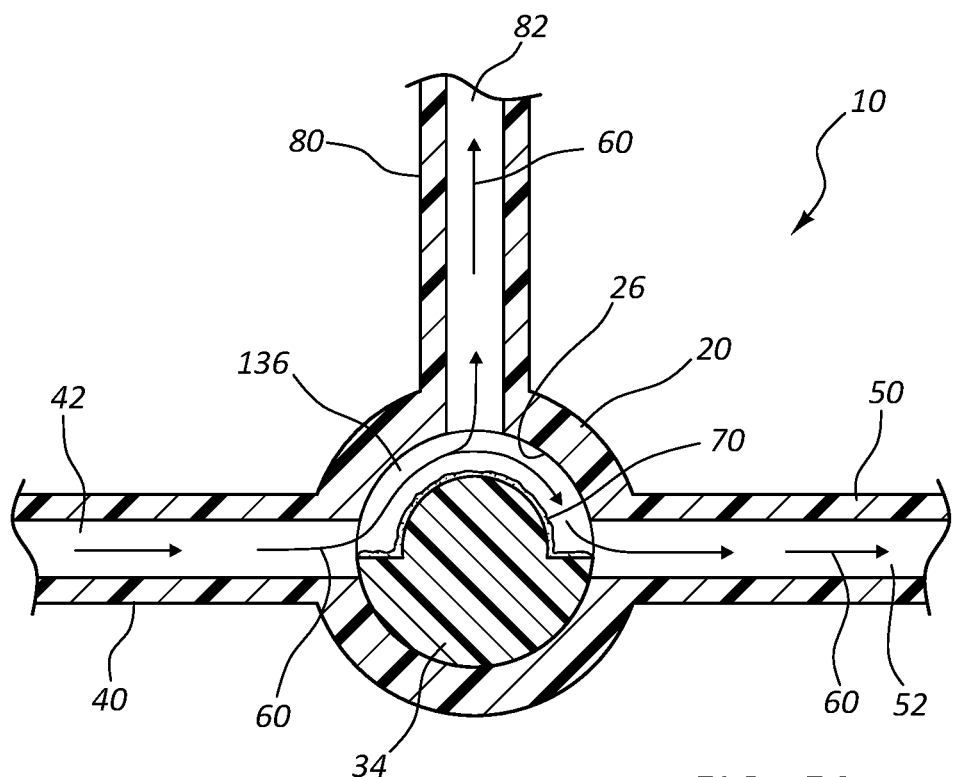
FIG. 5A shows a cross-section view of an antimicrobial stopcock medical connector having three ports in an open configuration in accordance with representative embodiments of the present invention.

Referring now to FIGS. 5A-5E, housing 20 may further include a middle port 80 that is positioned between upstream and downstream ports 40 and 50 and comprises a hollow interior 82 that is in fluid communication with lumen 26. In some instances, shaft 34 comprises a single fluid channel 136 having a length that is greater than half the circumference of shaft 34. As such, shaft 34 may be axially aligned within lumen 26 of housing 20 such that fluid channel 136 is in simultaneous contact with hollow interiors 42, 52 and 82 of ports 40, 50 and 80, respectively, as shown in FIG. 5A. In this position, fluid 60 is permitted to bypass shaft 34 and freely flow through the ports. Fluid channel 136 further comprises an antimicrobial coating 70 which is contacted by fluid 70 as fluid 70 passes through fluid pathway 136.

Figure 5B:
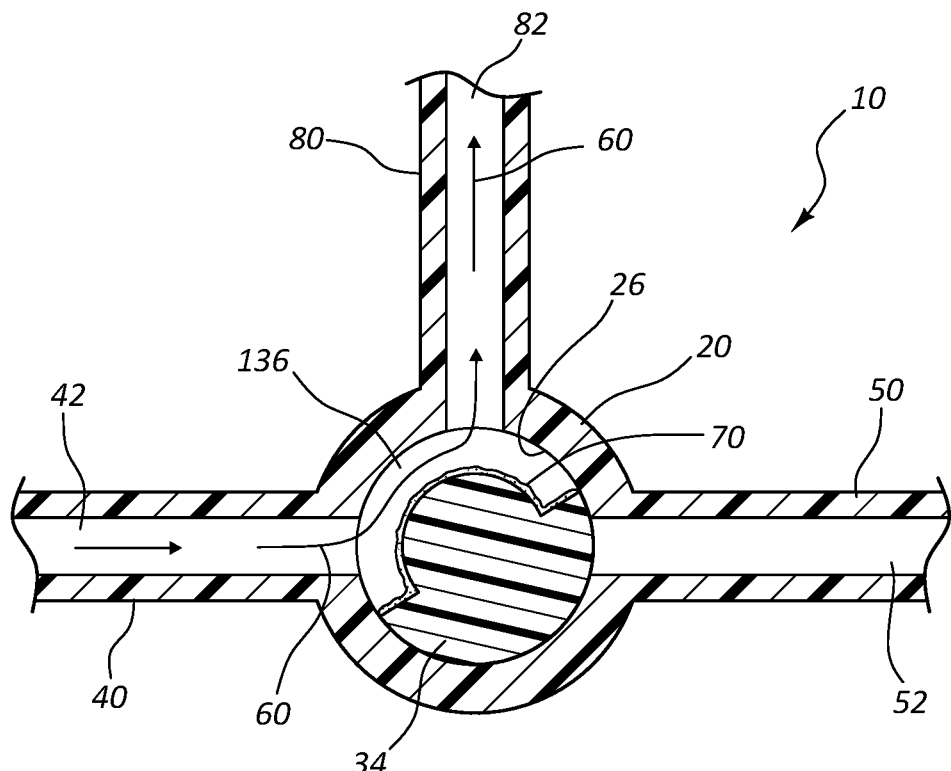
FIG. 5B shows another cross-section view of the antimicrobial stopcock medical connector of FIG. 5A having the three ports in open or closed configurations in accordance with representative embodiments of the present invention.
Figure 5C:
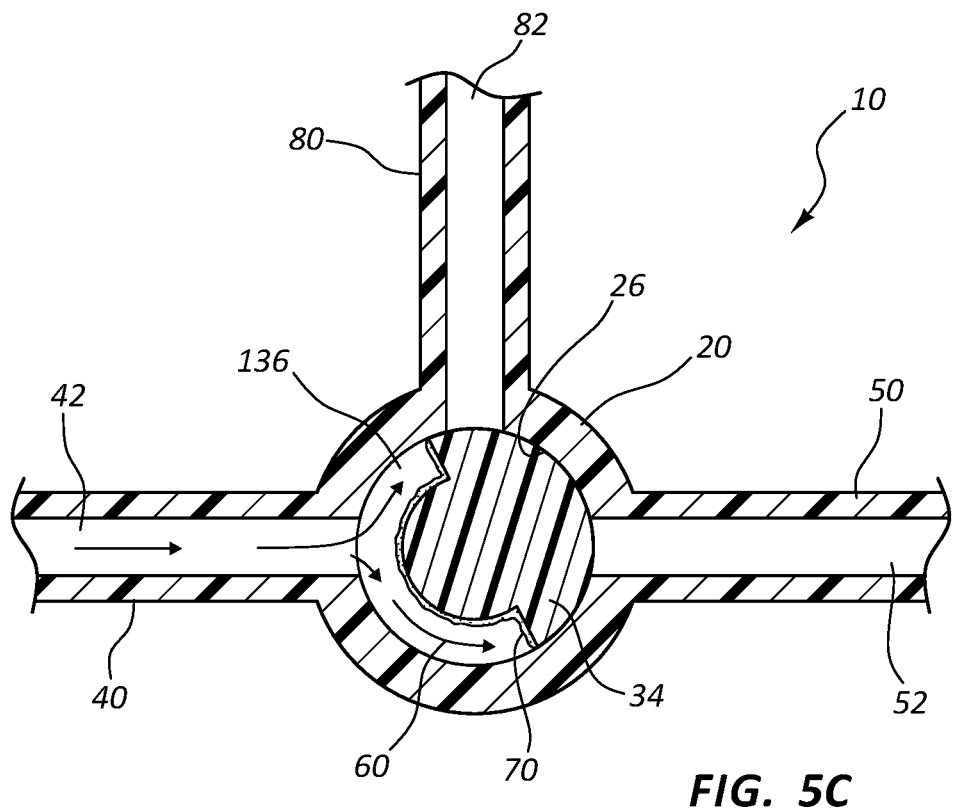
FIG. 5C shows another cross-section view of the antimicrobial stopcock medical connector of FIG. 5A having the three ports in open or closed configurations in accordance with representative embodiments of the present invention.

In some instances, shaft 34 is rotated counter-clockwise whereby fluid channel 136 is in fluid communication solely with upstream and middle ports 40 and 80, as shown in FIG. 5B. Thus, fluid 60 is prevented from flowing into downstream port 50. Upon further rotation of shaft 34 in a counter-clockwise direction, fluid channel 136 is placed in fluid communication solely with upstream port 40, as shown in FIG. 5C. As such, fluid 60 is prevented from flowing into downstream and middle ports 50 and 80. Fluid 60 within upstream port 40 and fluid channel 136 is stopped, whereby fluid 60 remains in contact with antimicrobial coating 70 thereby preventing microbial colonization within lumen 26.

Figure 5D:
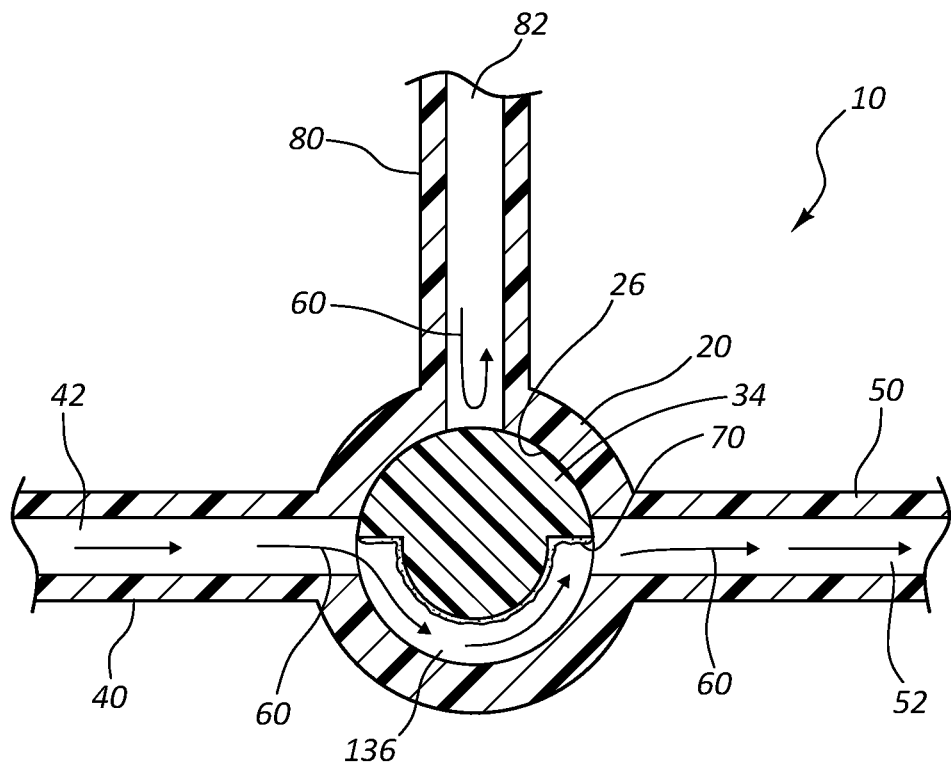
FIG. 5D shows another cross-section view of the antimicrobial stopcock medical connector of FIG. 5A having the three ports in open or closed configurations in accordance with representative embodiments of the present invention.

In some instances, as shaft 34 is further rotated in a counter-clockwise direction, fluid channel 136 is position such that fluid channel 136 is in fluid communication solely with upstream and downstream ports 40 and 50, as shown in FIG. 5D. Thus, fluid 60 is permitted to flow freely between upstream and downstream ports 40 and 50, yet is prevented from flowing into middle port 80. Antimicrobial coating 70 is contacted by fluid 60 as fluid 60 passes through fluid channel 136.

Figure 5E:
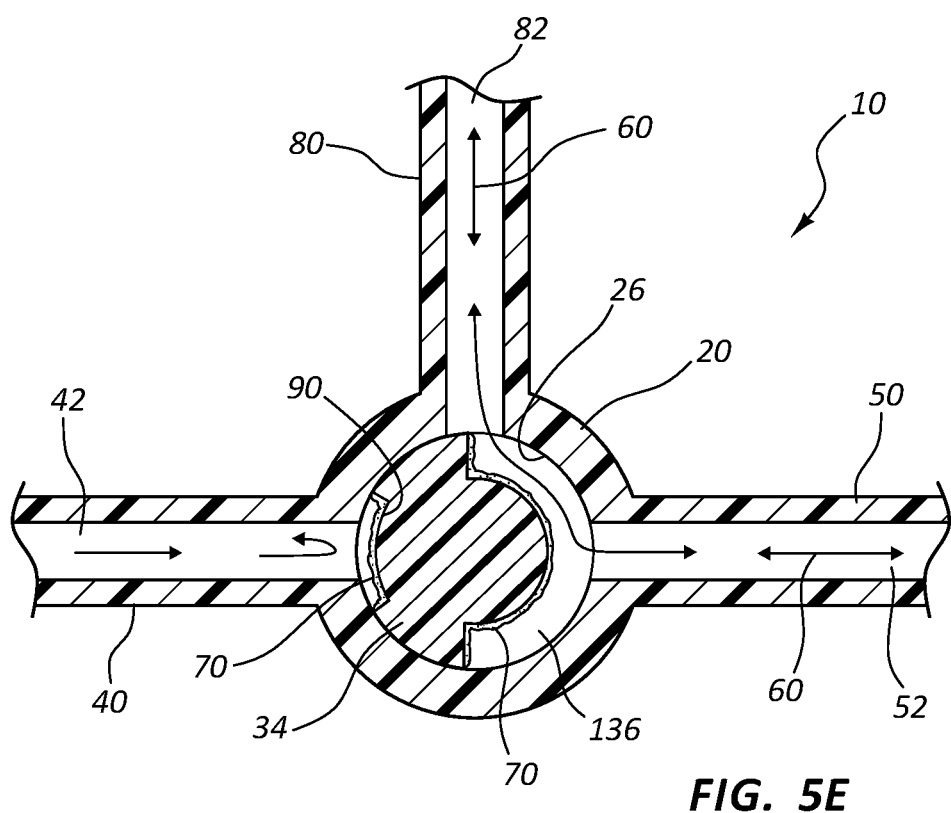
FIG. 5E shows another cross-section view of the antimicrobial stopcock medical connector of FIG. 5A having the three ports in open or closed configurations in accordance with representative embodiments of the present invention.

Upon further rotation of shaft 34 in a counter-clockwise direction, fluid channel 136 is in fluid communication solely with downstream and middle ports 50 and 80, as shown in FIG. 5E. Thus, fluid 60 may freely flow between downstream and middle ports 50 and 80, yet is prevented from flowing into upstream port 40. Fluid 60 flowing through fluid pathway 136 contacts antimicrobial coating 70, thereby preventing microbial growth and/or colonization, as discussed previously.

In some instances, shaft 34 further comprises an antimicrobial groove 90 that is positioned opposite fluid channel 136. Antimicrobial groove 90 comprises an antimicrobial coating in accordance with those materials discussed previously. Groove 90 is positioned on the outer surface of shaft 34 to align with one or more ports that are not in alignment or fluid communication with fluid channel 136. In other words, groove 90 is configured to be in fluid communication with one or more ports that are in an "off" position. As such, fluids within the respective ports are exposed to the antimicrobial material in groove 90, thereby preventing microbial growth or colonization within the ports while in the "off" position. As shown in FIG. 5E, antimicrobial groove 90 is aligned and in contact with upstream port 40 when ports 50 and 80 are in contact with fluid channel 136. Thus, fluid 60 within all ports is exposed to antimicrobial agent 70 regardless of the "on" or "off" position of shaft 34 and the respective ports.

Some embodiments of the present invention further comprise a tap component for use with a stopcock medical connector. In some instances, a tap component is provided which comprises a first end having a handle, a second end opposite the first end, and an outer surface interposed therebetween. The outer surface further comprises a fluid channel forming a groove, as discussed above. When inserted within a stopcock medical connector, the fluid channel forms a fluid pathway between the outer surface and a surface of the stopcock medical connector. For example, in some instances a fluid pathway is provided between the outer surface of the tap component and the inner surface of the stopcock medical connector housing. The fluid channel and fluid pathway thereby enable a fluid to bypass the tap component and flow through the stopcock medical connector.

The tap component may further include an antimicrobial agent applied to the fluid channel, wherein a fluid passing through the fluid channel contacts the antimicrobial material. The tap component may further include an antimicrobial groove formed in the outer surface and positioned such that the antimicrobial groove is in fluid communication with at least one port of the stopcock medical connector when in a closed position. The fluid channel may further comprise a length that is less than the circumference of the outer surface.

One having skill in the art will appreciate that the various other embodiments of the present invention may similarly be coated with an antimicrobial lubricant, thereby further adding a contact kill effect to the device. Various embodiments of the present invention may further be manufactured according to know methods and procedures. In some instances, an antimicrobial component is comprised of an antimicrobial material. In other instances, an antimicrobial component is extruded or molded of base polymer materials that have good bond strength to an antimicrobial material or agent, such as polycarbonate, copolyester, ABS, PVC, and polyurethane. The base polymer structure may be coated with an adhesive-based antimicrobial material, which may have elution characteristics. In some instances, the topology and dimensions of the base polymer structure are optimized for microbiology efficacy, lasting elution profiles, and assembly geometry constraints.

Various antimicrobial components of the instant invention may be casted or molded directly of antimicrobial material. In some instances, the antimicrobial component is casted in plastic and subsequently coated with an antimicrobial material. In some embodiments, an antimicrobial component is grown directly onto another component of the device. In other instances, various components of the device are joined together via an adhesive or epoxy. Antimicrobial components and coatings of the instant invention may be comprised of one or multiple antimicrobial agents in a polymer matrix. The polymer matrix may be adhesive-based, with a preference to acrylate- or cyanoacrylate-based adhesives for good bond strength and fast elution rates. Solvents may be added to increase bonding. Non-limiting examples of suitable antimicrobial material compositions are provided in United States Published Patent Application Nos. 2010/0137472, and 2010/0135949, each of which is incorporated herein by reference in their entireties.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A stopcock medical connector, comprising:
    a housing, comprising:
        an upstream port;
        a downstream port opposite the upstream port, wherein the housing includes no more than two ports, wherein the two ports include the upstream port and the downstream port; and
        a lumen extending between the upstream port and the downstream port; and
    a tap seated within the lumen, wherein the tap comprises an annular shaft, wherein an outer surface of the annular shaft comprises a first groove opposite a second groove, wherein the annular shaft is rotatable between a first position and a second position 90° from the first position, wherein in response to the annular shaft being in the first position, the annular shaft forms a fluid tight seal between the upstream port and the downstream port, wherein in response to the annular shaft being in the second position, the annular shaft is configured to allow fluid to flow between the upstream port and the downstream port within the first groove and the second groove, wherein the first groove and the second groove comprise an antimicrobial coating, wherein the annular shaft is seated within the lumen such that the annular shaft contacts a first groove of the housing and a second groove of the housing opposite the first groove of the housing, wherein a depth of the first groove of the annular shaft is greater than a depth of the first groove of the housing and a depth of the second groove of the annular shaft is greater than a depth of the second groove of the housing, such that in response to the annular shaft being in the second position, the annular shaft is configured to allow fluid to flow between the upstream port and the downstream port within the first groove and the second groove.

2. The stopcock medical connector of claim 1, wherein a cross-sectional area of the first groove, excluding an area of the antimicrobial coating of the first groove, combined with a cross-sectional area of the second groove, excluding an area of the antimicrobial coating of the second groove, is equal to a cross-sectional area of the upstream port or the downstream port.

* * * * *